United States Patent
Mauck

(10) Patent No.: US 6,906,453 B2
(45) Date of Patent: *Jun. 14, 2005

(54) METHOD AND APPARATUS FOR SIMULTANEOUSLY DEPOSITING AND OBSERVING MATERIALS ON A TARGET

(75) Inventor: Michael Mauck, Portland, OR (US)

(73) Assignee: Coincident Beams Licensing Corporation, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/842,899

(22) Filed: May 10, 2004

(65) Prior Publication Data

US 2004/0207308 A1 Oct. 21, 2004

Related U.S. Application Data

(63) Continuation of application No. 10/429,067, filed on May 2, 2003, now Pat. No. 6,815,880, which is a continuation of application No. 10/213,828, filed on Aug. 6, 2002, now Pat. No. 6,611,087, which is a continuation of application No. 09/608,908, filed on Jun. 30, 2000, now Pat. No. 6,522,056.
(60) Provisional application No. 60/142,147, filed on Jul. 2, 1999.

(51) Int. Cl.⁷ ............................................... H05H 7/06
(52) U.S. Cl. ............................. 313/359.1; 313/361.1; 250/396 R; 250/298; 315/500; 315/507; 315/111.61
(58) Field of Search .......................... 313/359.1, 361.1; 250/396 R, 298; 315/500, 507, 111.61

(56) References Cited

U.S. PATENT DOCUMENTS

| | | |
|---|---|---|
| 2,161,466 A | 6/1939 | Henneberg |
| 3,660,658 A | 5/1972 | Leboutet et al. |
| 4,760,261 A | 7/1988 | Rose et al. |
| 5,254,417 A | 10/1993 | Wada |
| 5,319,207 A | 6/1994 | Rose et al. |
| 5,336,891 A | 8/1994 | Crewe |
| 5,449,914 A | 9/1995 | Rose et al. |
| 6,522,056 B1 * | 2/2003 | Mauck ..................... 313/359.1 |

OTHER PUBLICATIONS

Michael Stewart Mauck, "*Correction of Chromatic Aberration With an Electron Mirror*" Portland State University, Portland, OR 97207, USA, 1992, pp. 79.

G.F. Rempher, et al, "*Correction of Chromatic Aberration With An Electron Mirror*". Portland State University, Portland, OR 97207, USA, 1992, pp. 3–8.

FEI and Philips . . . Global Vision, Focused Solutions, "*A New Generation of Process Control Tools*", FEI Company, 1997, pp. 1–2.

Mauck Systems, "*Optical Properties of Electrostatic Lenses*", Mar. 10, 1996; pp. 93–94.

G.F. Reppher, et al., "*An Experimental Study of the Hyperbolic Electron Mirror*", Portland State University, Portland, Oregon 97207, pp. 17–18; at least one year prior to filing date.

G.F. Rempher, "*Choice of Parameters*", Journal of App. Physics, vol. 67, No. 10, May 15, 1990.

Particle Accelerators and the Standard Model, "*The Cern Collider, the Fermilab Tevatron, the the Electroweak Bosons*", pp. 115–118; at least one year prior to filing date.

F.M. Charbons, "Field Emission"; at least one year prior to filing date.

* cited by examiner

*Primary Examiner*—Nikita Wells
(74) *Attorney, Agent, or Firm*—Chernoff, Vilhauer, McClung & Stenzel

(57) ABSTRACT

A system for joining at least two beams of charged particles that includes directing a first beam along a first axis into a field. A second beam is directed along a second axis into the field. The first and second beams are turned, by interaction between the field and the first and second beams, into a third beam directed along a third axis.

17 Claims, 12 Drawing Sheets

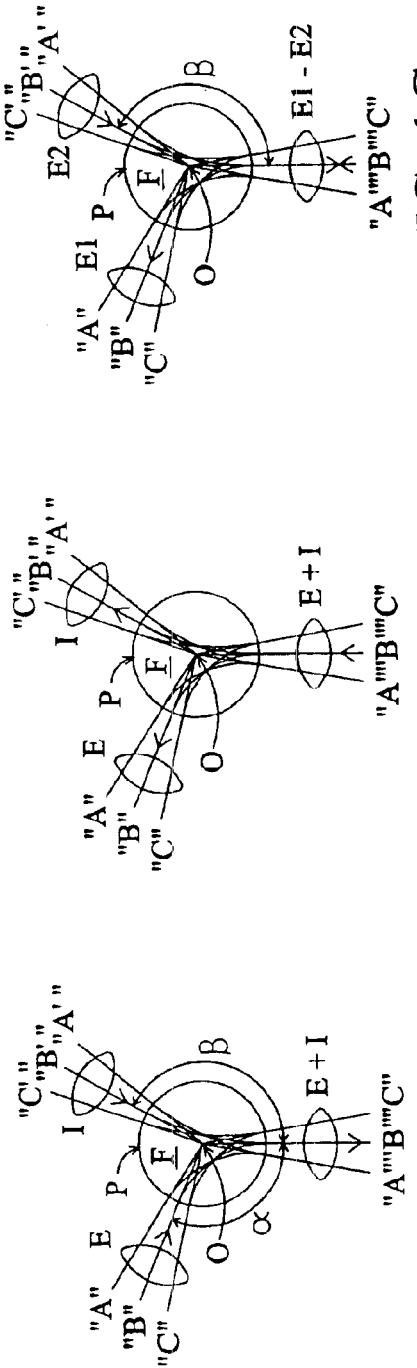
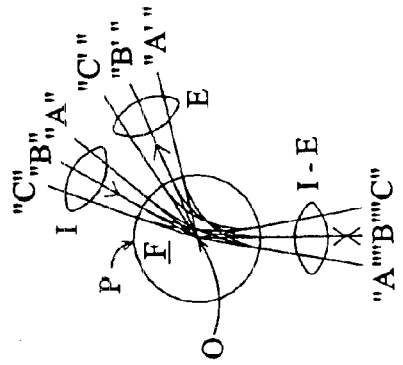
FIG. 1A  FIG. 1B  FIG. 1C
FIG. 1D  FIG. 1E  FIG. 1F

METHOD AND APPARATUS FOR SIMULTANEOUSLY DEPOSITING AND OBSERVING MATERIALS ON A TARGET

CROSS-REFERENCE TO RELATED APPLICATIONS

This application is a continuation of U.S. application Ser. No. 10/429,067 filed May 2, 2003, now U.S. Pat. No. 6,815,880, which is a continuation of U.S. application Ser. No. 10/213,828 filed Aug. 6, 2002 now U.S. Pat. No. 6,611,087 which is a continuation of U.S. application Ser. No. 09/608,908, filed Jun. 30, 2000, now U.S. Pat. No. 6,522,056 which claims the benefit of 60/142,147 filed Jul. 2, 1999.

BACKGROUND OF THE INVENTION

One aspect of the present invention relates to a system for depositing—e.g. "writing"—materials on a target while simultaneously monitoring—e.g. "reading"—the deposition process.

Beam Joining in a Magnetic Field

It is well known that passing beams of unfocussed charged particles through a magnetic field causes the constituent particles to separate according to particle charge-to-mass ratio and/or velocity. This is the basic principle of mass spectroscopy. A byproduct of the passage of such a beam through a magnetic field is the introduction of uncorrectable resolution-limiting aberrations to any subsequent images in the beam.

Rempfer and Mauck in a paper entitled Correction of Chromatic Aberration with an Electron Mirror, Optik Vol 92, No 1, (1992), disclosed that an image could be passed through a cylindrical magnetic turning field (CMTF) without limiting resolution if a real image were formed at the center of the magnetic field. In other words, the beam incident on the CMTF is focused at its center and thus may be refocused by a lens back to a single image without loss of resolution. Such a geometry is not useful for mass spectrometry because subsequent images in the beam are not easily separated by ion mass as they are in a system where the ions pass through a magnetic field substantially collimated. In other words, a mass spectrometry system uses an unfocused beam incident on the magnetic field. Then the beam normally passes through a lens and is separated into different ion masses.

FEI Company sells an XL800 Full Wafer Scanning Microscope which uses an ion beam for eroding—"machining"—a surface, and an electron beam for probing and monitoring the progress of erosion. The two beam-forming structures are separate but physically proximate one another.

Chromatic and Spherical Aberration Correction

Just as light beams passed through optical lenses will experience resolution-limiting spherical and chromatic aberrations, so beams of charged particles passed through electrostatic and electromagnetic lenses also include these aberrations, due primarily to two factors:

1. spherical aberrations are due to the failure of a lens to focus particles at different lateral distances from the axis thereof to the same point longitudinally on the axis, i.e., for a converging lens and particles incident upon the lens parallel to the axis, particles farther from the axis are focused nearer the lens than particles closer to the axis; and 2. chromatic aberration are due to the failure of a lens to focus particles of different energies to the same point on the axis.

Chromatic and spherical aberration may also be introduced into electron optical systems from the sources of the beams. Where energy aberration becomes significant, it can be reduced by passing the beam through an energy filter at the expense of reduced beam current.

Henneberg, U.S. Pat. No. 2,161,466, teaches that the aberrations of electrostatic mirrors have the opposite sign from those of electrostatic and electromagnetic lenses, and that such mirrors could in principle be used to correct spherical and chromatic aberrations of lens systems and beam sources. Rempfer and Mauck, Optik, 1992 discovered that incident and reflected beams of charged particles could be separated if the single homogenous beam is focused upon and passed through the geometric center of a substantially cylindrically symmetrical magnetic field, where the field is located at an image plane of a particle beam lens. In that system, two lenses were used to relay an image between each deflecting field, and small magnetic beam deflection angles were necessary in order to prevent magnetic field distortion effects. Unfortunately, such a system is complicated and the deflection angles are small. Further, small deflection angles cause distortion in the beam exiting the magnet.

Hereinafter, the term "incident beam" refers to a beam of charged particles which is directed toward an element which modifies it in some way.

Hereinafter, the term "reflected beam" or "exiting beam" refers to a beam of charged particles which has been modified in some way by interaction with some element.

Magnetic Deflection of 127 Degrees or 135 Degrees

Leboutet et al., U.S. Pat. No. 3,660,658, disclose a mass separator using a magnetic deflector system which deflects a charged particle beam at an angle of 90 degrees to its initial axis, and which also includes a magnetic deflector which deflects the beam at an angle of 127 degrees. The particle beam of Leboutet et al. passes through the turning magnetic field unfocussed. The Leboutet et al. device relies on the unfocussed nature of the beam to perform the mass separation.

Rose et al., U.S. Pat. No. 4,760,261, disclose an electron energy filter which operates at a preferred angle of 115 degrees. The geometry of Rose et al. incorporates a triangular-shaped magnet. Like Leboutet et al., Rose et al. depend upon separating all but those particles within a narrow selected energy range from a beam of particles having a wide spectrum of energies. Such a device is effective only when using unfocused beams.

Crewe, U.S. Pat. No. 5,336,891, discloses an aberration-free lens system which includes both magnetic and electrostatic components to obtain aberration-free imaging. All examples disclosed by Crewe (FIGS. 3a–3i) show deflections only of 45 degrees, 90 degrees, and 180 degrees.

Rose et al., U.S. Pat. No. 5,449,914, disclose an energy filter in which the beam is deflected four time at angles of 135 degrees. Rose et al. relies on an unfocused beam to perform its functionality.

Electrostatic Mirror Used with Magnetic Deflector

Wada, U.S. Pat. No. 5,254,417, discloses a reflection mask for producing reflected electrons from the surface of a substrate in a desired pattern. An electron beam is deflected by an electromagnetic field into an electrostatic mirror, from which it is reflected back into the field and deflected to continue in its former direction. Wada does not focus its incident or its reflected particle beams at the geometric center of the respective magnetic deflecting fields.

Rose et al., U.S. Pat. No. 5,319,207, disclose an electron beam passing through magnetic deflection fields B1/B2, deflected 90 degrees into a mirror, reflected back through the magnetic deflector, and deflected 90 degrees onto the object to be scanned. The magnetic deflector taught by Rose et al. is a complex device formed by a pair of circular magnetic poles having sufficient separation therebetween to allow one or more beams of charged particles to pass therethrough. Rose et al. focus their incident beam on the hypothetical diagonal symmetry plane 3g of deflector 3, and their reflected beam on the hypothetical diagonal symmetry plane 3h.

Combination of Electrostatic Mirror and Cylindrical Magnetic Turning Field

Rose et al., U.S. Pat. No. 5,319,207, further disclose an electron beam passing through magnetic deflection fields B1/B2, deflected 90 degrees into an electrostatic mirror, reflected back through a square magnetic deflector, and deflected 90 degrees onto the object to be scanned. Rose et al. focus their incident and reflected particle beams on hypothetical diagonal symmetry planes. Further, the deflector of Rose et al. is square, and has two magnetic fields which must be adjusted and balanced for strength.

What is desired, is a system for depositing—e.g. "writing"—materials on a target while simultaneously monitoring—e.g. "reading"—the deposition process.

SUMMARY OF THE INVENTION

The present inventions, in several aspects, overcome the aforementioned drawbacks of the prior art by providing a system for joining at least two beams of charged particles that includes directing a first beam along a first axis into a magnetic field. A second beam is directed along a second axis into the magnetic field. The first and second beams are turned, by interaction between the field and the first and second beams, into a third beam directed along a third axis.

In another aspect of the present invention a system separates at least two beams of charged particles by directing a first beam along a first axis into a magnetic field where the first beam includes mixed charged particles. The first beam is directed at the magnetic field. The mixed charged particles are separated into at least a second beam and a third beam, by interaction between the magnetic field and the first beam.

In another aspect of the present invention a system turns at least two beams of charged particles by directing a first beam along a first axis into a magnetic field where the first beam exits the magnetic field along a second axis. A second beam is directed along a third axis into the magnetic field where the second beam exists the magnetic field along a fourth axis. The third axis is at least one of colinear and coaxial with the second axis and the second beam along the third axis has a different direction of travel than the first beam along the second axis.

In another aspect of the present invention a system focuses at least two beams by providing a first beam and a second beam that are coaxial with one another where the charge of the first beam is opposite from the charge of the second beam. The first beam and the second beam are directed through a lens such that the first beam and the second beam are focused at the same plane.

In another aspect of the present invention aberrations are reduced in a beam of charged particles by directing the beam along a first axis to a magnetic field where the beam leaves the magnetic field along a second axis that is not colinear with the first axis. The second axis is directed toward a mirror. The beam is reflected from the mirror along a third axis. The beam is reflected from the mirror along a third axis. The beam is directed along the third axis to the magnetic field where the beam leaves the magnetic field along a fourth axis that is not colinear with the first axis.

In another aspect of the present invention a system for depositing particles on a target and monitoring the depositing includes providing a first beam of ions, a second beam of electrons, and combining the first beam and the second beam into a coaxial third beam by interaction between the field and the first and second beams. The ions are deposited from the third beam on the target. The deposition is monitored with the electrons of the third beam.

In another aspect of the present invention a system for depositing at least one ionized atom on a target and moving the at least one atom into a desired position include at least one ionized atom from a first source that is directed to a magnetic field along a first axis, and toward the target along a second axis different from the first axis by interaction of the at least one ionized atom and the magnetic field. At least one electron from a second source is directed to the magnetic field along a third axis, and toward the target along a fourth axis by interaction of the at least one electron and the magnetic field. The at least one ionized atom is deposited on the target. The at least one electron is directed in such a manner as to move the deposited at least one ionized atom on the target to a desired position.

BRIEF DESCRIPTION OF THE DRAWINGS

FIGS. 1A–1F diagrammatically represent different interactions of beams of charged particles with a magnetic field.

DETAILED DESCRIPTION OF THE PREFERRED EMBODIMENT

Figure 2A:
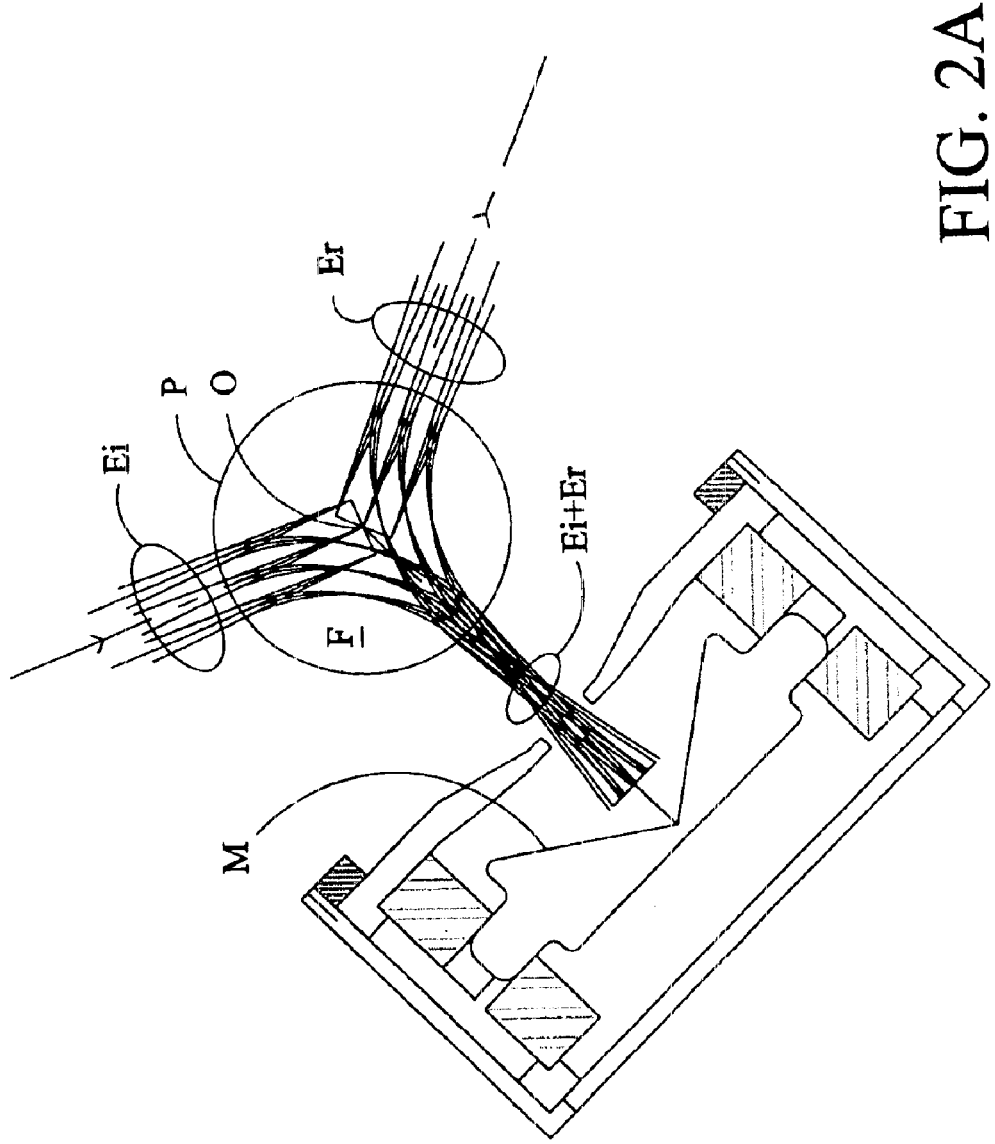
FIG. 2A is a diagrammatic representation of the simplified geometry of a magnetic field and mirror.

In light optics the beamsplitter is an element used to combine or separate beams. It may be a transparent substrate with one surface partially transmitting and partially reflecting. It may be placed in a beam of light at an angle to the beam so that the beam is separated into two parts. The coatings of the beamsplitter may be prepared so that the beam is separated into different wavelengths, intensities, and/or polarizations, as desired. The beam directions may likewise be referred to so that the separate beams are combined into a single coaxial beam. By analogy, in electron optics, there has not been a corresponding element to the beamsplitter. Accordingly, charged particle optical systems requiring the joining or separating of beams along a common axis, are not realizable.

To illustrate the limitations due to aberrations which should be dealt with for the preferred embodiment of the system of the present invention to work most effectively, consider the effect of an electrostatic mirror M on a beam of charged particles from object source S, which beam is passed through objective lens L1, having a magnification factor m1, and through compensating lens L2, having a magnification factor m2, to mirror M. Both objective lens L1 and compensating lens L2 will introduce both chromatic and spherical aberration to the image of source S on its incident path as well as on its reflected path back through L2 to the image plane of L1 from mirror M. Chromatic aberration is proportionate to the square of the product of m1, m2, and spherical aberration is proportionate to the fourth power of the product of m1, m2. Electrostatic mirror M will also introduce both chromatic and spherical aberration into the reflected image of source S but they will be of the opposite sign from those introduced by L1 and L2. By choice of the correct parameters for mirror M and magnification factors m1 and m2, both aberrations of the mirror may be set equal and opposite to cancel those aberrations introduced by L1 and L2. Consequently, the image of source S reflected back to the image plane of L1 by mirror M will be substantially aberration-free. Further, the mirror parameters can be adjusted to present a substantially over-corrected image at L1 which will correct for aberrations of a lens system preceding or following L1.

To simplify illustrating and understanding the functionality of the different aspects of the present invention, and in particular a cylindrical magnetic field, for turning beams of electrified particles, FIGS. 1A–2D are for the purpose of illustrating several different situations of particular interest.

Particle beams entering and leaving electric, electrostatic, magnetic, or electromagnetic elements may be modified in some manner, all of which are generically referred to herein as a field. Consequently, to more clearly distinguish the entering beam from the exiting beam, the entering beam will be referred to as the "incident" beam and the existing beam will be referred to as the "reflected", "exiting", or "leaving" beam.

In the following detailed discussions of the interaction of beams of electrically-charged particles with magnetic fields, beam E will represent an electron beam, and beam I will represent positive or negative ion beams. The beams are preferably focused at the geometric center O of a cylindrically symmetrically uniform magnetic turning field F, and will appear to be emanating from the center O after having traversed field F. The field F may be substantially cylindrical, substantially symmetrical, and/or substantially uniform, as desired, through the remainder of the description herein. The beam may be focused at substantially the geometric center O, as desired, through the remainder of the description herein. It is also to be understood that any type, shape, field and/or charge distribution, of magnetic field may be employed, as desired, through the remainder of the description herein. It is further to be understood that the beam may be focused or unfocused and directed at the center or elsewhere, as desired, through the remainder of the description herein. Also, while many illustrations show only one or two beams, it is to be understood that any number of beams may be employed, as desired.

Some of the beams may be coaxial in nature, as desired. In addition, the beams may be colinear in nature, as desired. Beams where the particles are moving in the same direction are labeled as additive for convenience of illustration, i.e., E1+E2, I+E, etc. Beams where the particles are moving in the opposite directions are labeled as subtractive for convenience of illustration, i.e., I–E, I1–I2, etc.

Coaxial or colinear beams of differing charge and/or direction of motion will not affect one another to any measurable degree except for beneficial space charge neutralization possible in intense beams. Investigations into the nature of sub-atomic particles use physically massive particle accelerators accelerating enormous currents of counter-rotating particles to nearly the velocity of light, yet collisions between the particles are random and rare.

FIG. 1A illustrates the behavior of two charged particle beams E and I as they pass through field F, the circumference of which is indicated by P. Beam E includes rays "A", "B", and "C", the paths of which through F are traced by "A"—"A", "B"—"B", and "C"—"C", respectively. Beam I includes rays "A'", "B'", and "C'", the paths of which through F are traced by "A'"—"A'", "B'"—"B'", "C'"—"C'", respectively.

Beams E and I are preferably focused at the center O and emerge from field F as a combined beam E+I containing both particles intermingled coaxially, or colinearly, as desired. Combined beam E+I will appear to be emanating from the center O of field F.

The particles of beam E are less massive and/or have lower velocity than those of beam I, as indicated by the greater angle through which beam E is turned by field F, compared to the angle through which beam I is turned. In essence, FIG. 1A illustrates the joining of two oppositely charged particle beams into a single beam.

FIG. 1B is a diagrammatic representation of incoming coaxial (or colinear) beam E+I, which is preferably focused at the geometric center O of magnetic field F. It is to be understood that the beam may be focused at other portions of the magnetic field, especially dependent on the geometry of the magnetic field. Magnetic field F is preferably oppositely directed from field F of FIG. 1A. The beam preferably includes mixed charged particles, such as for example, different charge to mass ratio, different charges, and/or different energies.

The paths of rays "A", "B", and "C" of beam E are indicated by "A"—"A", "B"—"B", and "C"—"C", respectively. The paths of rays "A'", "B'", "C'" of beam I are indicated by "A'"—"A'", "B'"—"B'", and "C'"—"C'", respectively. The individual particles are separated according to well-known physical principles as they pass through magnetic field F. In essence, FIG. 1B illustrates the separation of a mixed beam of oppositely charged particles into two distinct particle beams.

FIG. 1C is a diagrammatic representation of a beam E1–E2 of similarly charged particles, such as electrons, traveling in different, such as opposite, directions. Magnetic field F is preferably oriented similarly to that shown in FIG. 1B. Beam E1 is incoming from below and exits to the left, above. Beam E2 is incoming from the right, above, and exits below, with E1 but in the opposite direction. Preferably beam E1–E2 is a coaxial beam, but may also be colinear. Both beams are preferably focused at the center O as they enter magnetic field F, and both appear to be emanating from center O as they exit.

The paths of rays "A", "B", and "C" of beam E1 through field F, incoming from the bottom, are traced by "A"—"A", "B"—"B", and "C"—"C", respectively. The paths of "A'", "B'", and "C'" through field F, incoming from the top right, are indicated by "A'"—"A", "B'"—"B", and "C'"—"C", respectively. In essence, FIG. 1C illustrates the mixing of three beams.

FIG. 1E is a diagrammatic representation of a beam I1+I2 of charged particles having the same sign, with different charge-to-mass ratios, and/or different velocities. Beam I1+I2 enters from the bottom and, when passed through the turning field F, I1 particles are separated from I2 particles because I1 particles are less massive or lower velocity than I2 particles and therefore will be turned more sharply.

Beam I1+I2 includes rays "A", "B", and "C". The paths of I1 through field F are traced by "A"—"A", "B"—"B", and "C"—"C", respectively. The paths of I2 are traced by "A"—"A'", "B"—"B'", and "C"—"C'", respectively. It is noted that by reversing the direction of the beams, FIGS. 1D and 1E illustrate the behavior of beam I1 and I2, and the deflections are opposite thereto because the particle velocities is reversed. In essence, FIG. 1E illustrates the separation of one particle beam including multiple similarly charged particle beams into separate beams.

FIG. 1F is a diagrammatic representation of two beams I and E having the same sign charge-to-mass ratios, but with different masses and traveling in opposite directions. Both joining and separating the two beams is accomplished simultaneously. Beam I is incoming from the right above, and beam E is incoming from below magnetic field F, where I–E is preferably coaxial (or colinear), with the particles moving in different directions.

Beam I–E includes rays "A", "B", and "C". The paths of beam I through field F are traced "A"—"A", "B"—"B", and "C"—"C", respectively, and the paths of beam E through field F are traced "A"—"A'", "B"—"B'", and "C"—"C'", respectively. In essence, FIG. 1F illustrates the mixing of three similarly charged particle beams.

In the following detailed discussions of the interaction of beams of electrically charged particles with magnetic field F, such as a cylindrically uniform magnetic turning field, and electrostatic mirror M, beam E particles are electrons, beam I particles are positively charged ions, and incident beams are preferably focused at the geometric center O of the turning field F. Beams exiting from the field F appear to be emanating from enter O thereof, and beams reflected from mirror M are preferably focused at the center O of field F.

Figure 9:
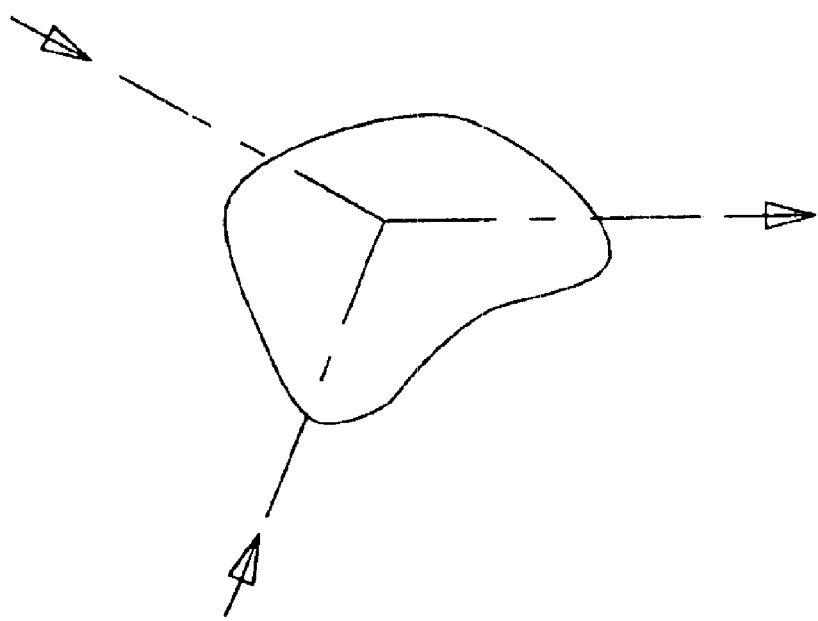
FIG. 9 represents a generic magnetic and/or electric field interacting with multiple beams.

FIG. 9 illustrates the interaction of a plurality of beams with a generic field, such as a field that is electric and/or magnetic. The direction of the travel of the particles of the beams may be modified, as desired.

Figure 8:
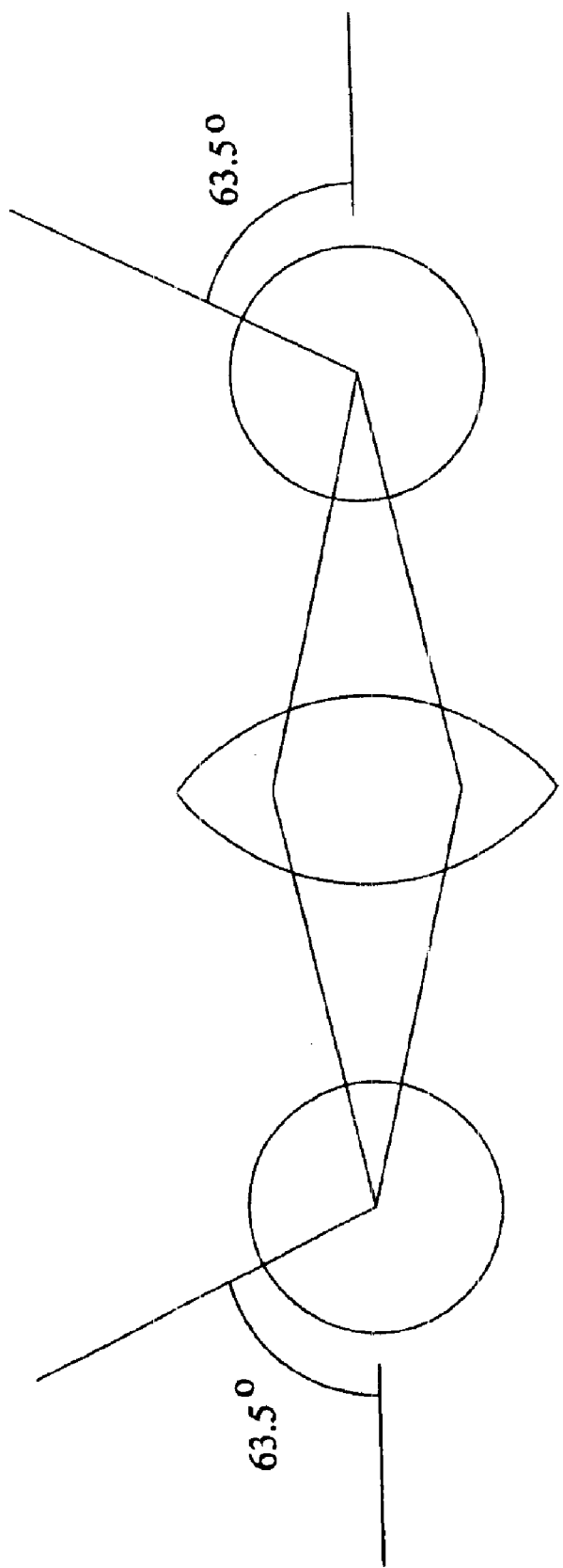
FIG. 8 represents an interaction of beams with an electrostatic or magnetic field.

FIG. 8 illustrates the passage of a beam through a pair of fields, such as magnetic fields, and a lense combination. The entering beam is preferably focused at the geometric center of and turned by the magnetic field. The beam is incident upon a lens. The lens then focuses the beam which again is focused preferably at the geometric center of another magnetic field. The resulting beam is identical to the incident beam. The preferred angle of turning is 63.5 degrees (of substantially 63.5 degrees) for a total of 127 degrees (or substantially 127 degrees).

FIG. 2A is an idealized diagrammatic representation of the interaction of incident beam Ei with magnetic field F and electrostatic mirror M. Mirror M may have any suitable surface, such as a flat planar surface or a concave surface, as shown, depending upon the amount of corrective spherical and chromatic aberration to be effected on incident beam Ei. Beam Ei, focused on the center O of magnetic field F, the effective periphery of which is indicated by P, enters field F from the upper left. Field F turns incident beam Ei to the right (as viewed along the direction of the beam) into mirror M, from which it is reflected as beam Er and focused on geometric center O of field F.

It is noted that the incident beam Ei and reflected beam Er are preferably coaxial and/or colinear between mirror M and field F, even though beam Ei-Er particles are moving in opposite directions.

Reflected beam Er is again turned to the right (as viewed along the direction of Er particle movement) by field F, effectively separating it from incident beam Ei for further beam manipulation.

It is to be understood that the turning angle of the incident beam is equal to the turning angle of the reflected beam. This turning angle has useful optical effects upon the beam traversing the assembly.

Figure 2B:
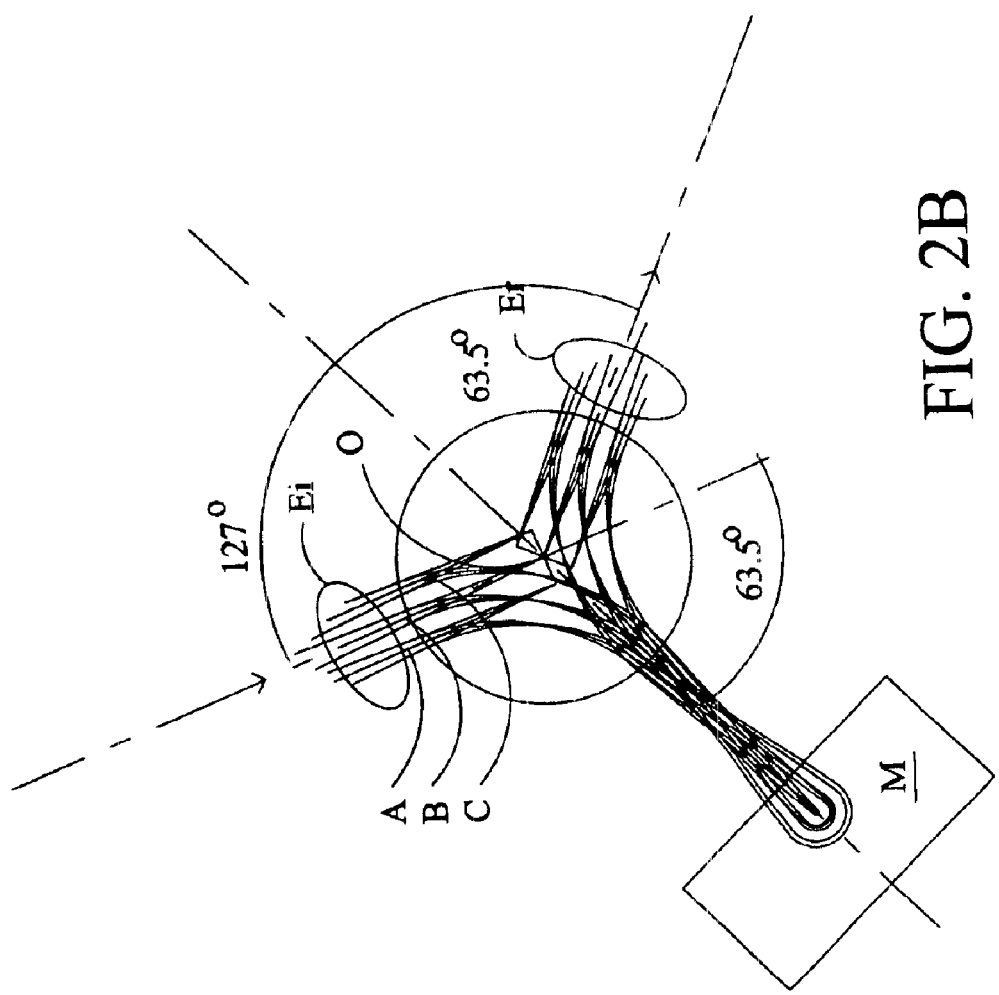
FIG. 2B is a ray diagram of the paths of charged particles of FIG. 2A.

FIG. 2B is an idealized detailed diagrammatic representation of the interaction of incident beam E with magnetic field F and electrostatic mirror M. FIG. 2B and FIG. 2A both illustrate the inversion of the image that occurs when beam E is reflected from mirror M.

Three rays "A", "B", and "C" of incident beam Ei are shown as image Q of an arrow which is focused on the geometric center O of magnetic field F. However, as the beam is turned to the right toward mirror M, the image will appear to emanate from the geometric center O of field F. As beam Ei is reflected from mirror M (as beam Er), image Q will undergo an inversion and will be focused upon the center O of field F.

In FIG. 2B, it may be observed that the angle of first turning is 63.5 degrees (or approximately), and the angle of second turning is again 63.5 degrees (or approximately), making the apparent angle of turning, between incident beam Ei and reflected beam Er, 127 degrees (or approximately). These angles provide the advantage that, only at these angles, the primary rays from an extended image enter and exit from the field F/mirror M structure parallel to the axes of the incident and reflected beams, respectively. Other angles limit the field of view of the whole optical system by diverting the ray bundles away from the axis, thus preventing outer rays of the beam from passing through subsequent optical elements or systems. Use of these angles permits undeflected beams focused at the center of field F to be deflected and pass there through with minimum beam distortion and no loss of resolution. This feature is useful for independently deflecting the individual beams prior to joining them into a single coaxial beam, as described previously, so that the beams focused in the final image at the target may be independently manipulated.

Consequently, with the mirror arrangement disclosed in FIG. 2B, incident beam Ei will appear to have been turned 127 degrees to the left by magnetic field F, without image Q having been inverted in the process. One advantage of this arrangement is that mirror M can be adjusted to correct both the chromatic and the spherical aberrations caused by passage through any focusing lenses before and/or after turning and reflection shown in FIG. 2B.

Figure 2C:
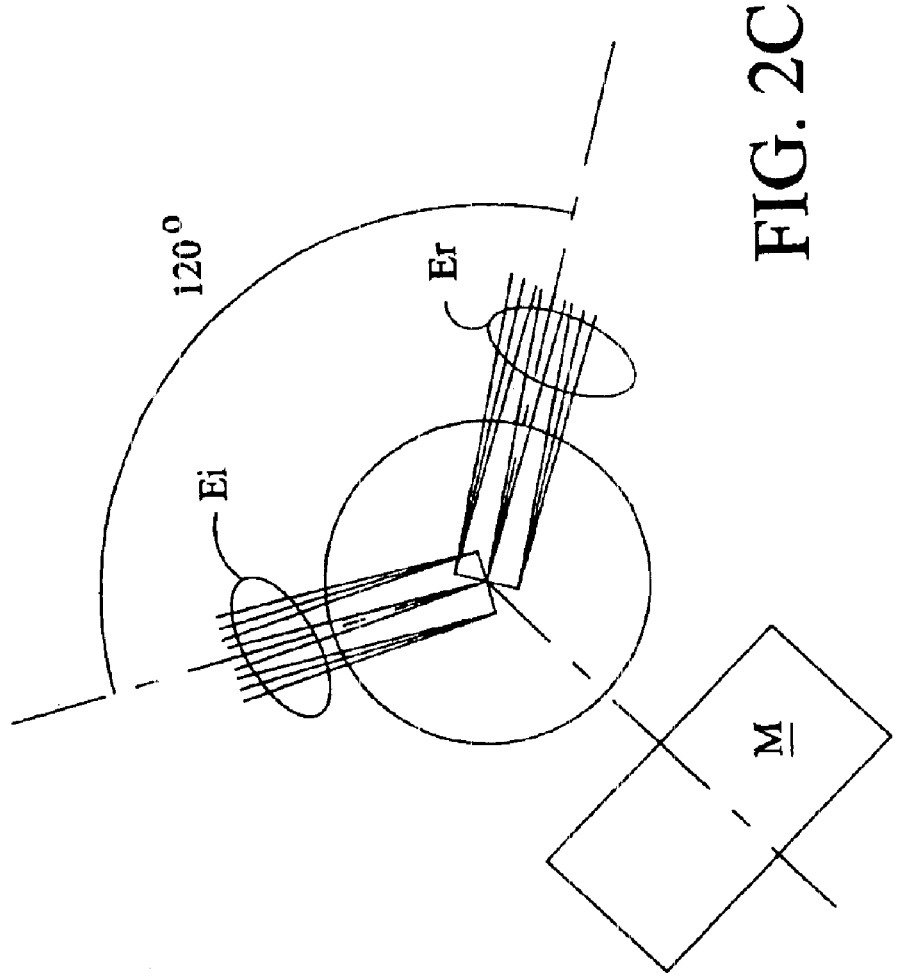
FIG. 2C is a ray diagram of the paths of charged particles in the geometry of FIG. 2B for angles less than 127 degrees.

FIG. 2C illustrates a ray diagram of the paths of charged particles in the geometry of FIG. 2B for turning angles less than 127 degrees. Here ray bundles are heading toward the beam axis.

Figure 2D:
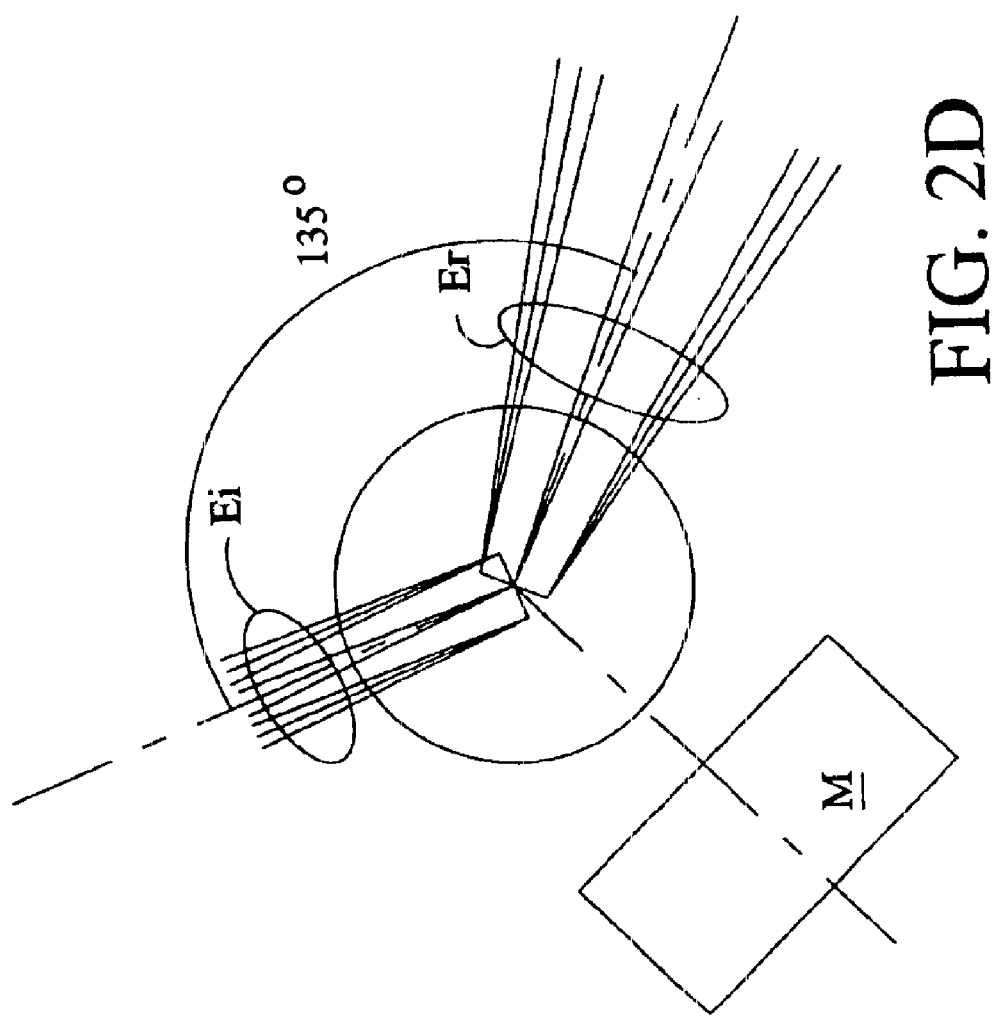
FIG. 2D is a ray diagram of the paths of charged particles in the geometry of FIG. 2B for angles greater than 127 degrees.

FIG. 2D illustrates a ray diagram of the paths of charged particles in the geometry of FIG. 2B for turning angles greater than 127 degrees. Here the ray bundles are diverging from the beam axis.

Figure 3:
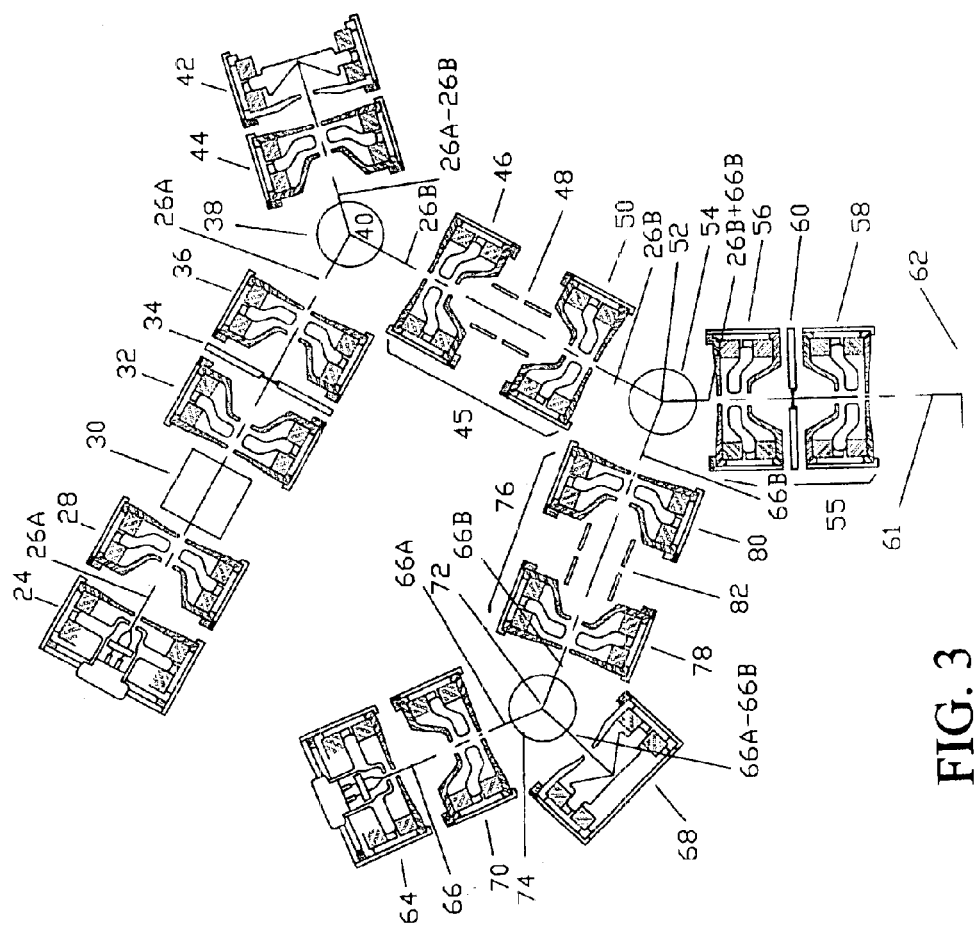
FIG. 3 is a simplified diagrammatic representation of a system for depositing ionic materials on a target and detecting with an electron beam the deposited ionic materials.

FIG. 3 is a simplified diagrammatic illustration disclosing the preferred structure for a complete system for depositing, or "writing", ionized molecular materials on a target, and for monitoring, or "reading", the materials as they are deposited or written, respectively. The drawing, while simplified as far as voltage supplies, supporting structures, controls, spatial, and angular relations, etc., discloses the individual components desired for the system.

For convenience of understanding, a beam will be described as turning to the "right" or "left" when viewed along, and in the direction of, the movement of the beam particles.

Ion source 24 emits an ionized beam 26a of the particular materials to be deposited, the nature of which is determined by the ultimate function to be performed. Ion source 24 may be a liquid metal ion source, if desired. Beam 26a is collimated by a lens 28, and the particular ions desired are selected by a mass filter 30.

A lens 32 focuses beam 26a on a mass-selecting aperture 34. The mass filter 30 and mass selecting aperture 34 may not be needed if the ion source used is composed of a single atomic isomer. The remainder of beam 26a is focused by lens 36 producing, with the selected ions, a real image of the source 24 at the a center 38 of a first magnetic turning field 40. First turning field 40 turns the charged incident beam 26a to the left into a first electrostatic mirror 42. A first relay lens 44 may be required to provide a magnified or demagnified image of the source 24 for a mirror 40 to act upon.

For clarity of description, incident beam 26a will be identified as reflected beam 26b after reflection from the mirror 42, although likely no substantive change in the beam 26a has occurred, other than reversal of the real image and correction (or overcorrection) by the mirror 42 of chromatic and spherical aberration caused by passage through lenses 28, 32, 36, and 44.

The mirror 42 produces a real, but reversed, image of the source at the center 38 of the first turning field 40 (with or without the influence of lens 44), by which the reflected beam 26b is directed to the left through collimating lens 46 into a beam deflector structure 48, as hereinafter described in greater detail in FIGS. 4 and 5. Deflected beam 26b is refocused at the geometric center 52 of second magnetic electromagnetic components, and their requirement for heavily regulated and smoothed, high current power supplies requires significantly more space and imposes significantly greater equipment and engineering costs than do electrostatic components.

However, the use of electromagnetic lenses and deflectors does not avoid the spirit or intent of the invention.

Reflected beam 26b is focused upon a geometric center 38 of a cylindrically symmetrical magnetic turning field 40. In turn, a lens 46 collimates turned beam 26b before it is passed through a beam deflector 48, and is thereafter focused by a lens 50 upon a geometric center 52 of a turning field 54. Turned and focused beam 26b is directed toward a desired destination, e.g., target 62 of FIG. 3, which may be any type of device such as an individual integrated circuit die, or a larger wafer.

The relay lens assembly 45 allows the beam 26b to be focused at the geometric centers 38 and 52 of both turning fields 40 and 54.

Second magnetic turning field 54 is a joining field, joining ion beam 26b to electron beam 66b in the preferred embodiment, as explained in greater detail later.

The beam 26b is turned to the left as it passes through the second field 54, and directed through beam focusing lenses 56 and 58 having a common aperture stop 60. Stop 60 and lenses 56 and 58 form a preferred combined beam-focusing system 58, generally referred to as a telecentric stop, as hereinafter described in greater detail. The beam 26b is coaxially joined by beam 66b, and directed and focused by lenses 56 and 58 preferably perpendicularly to, e.g., target 62, where a desired arrangement of ions is to be deposited.

The preferred embodiment of the present invention includes second beam forming and manipulating structure, for controlling, aligning, manipulating, and modifying, the electron beam 66. For clarity of explanation, reading beam 66 (known from FIGS. 1A–1F and 2A–2D as beam E) will be described as incident beam 66a before being diverted into mirror 68, and as reflected beam 66b after reflection therefrom. Incident beam 66a is emitted by electron source 64 which is, preferably, a well-known point source, e.g., a field emission cathode or a thermionic field emitter. Beam 66a is collimated and focused by lens 70 to the geometric center 72 of third turning field 74, and turned to the right into second electrostatic mirror 68, which may be concave for greater correction of chromatic and spherical aberration. Reflected beam 66b is focused by the mirror 68 to the geometric center 72 of the third field 74, and again turned to the right into preferred deflecting and focusing assembly 76, which includes collimating lenses 78 and 80, and deflecting plate structures 82, as hereinafter explained in greater detail in connection with FIGS. 4 and 5. The lens 78 is focused on the geometric center 72 of the third turning field 74, and lens 80 is focused on the geometric center 52 of the second turning field 54. Beam 66b is turned to the right by field 54, so that it is coaxial with ion beam 26b, and focused perpendicularly to, and incident on, target 62.

The geometry of turning fields 40, 54, and 74 preferably deflects beams 26a, 26b and 66a, 66b through an angle of 63.5 degrees.

A reflected beam 66b is focused upon a geometric center 72 of a cylindrically symmetrical magnetic turning field 74. In turn, a lens 78 collimates turned beam 66b before it is passed through beam deflectors 82, and is thereafter focused by a lens 80 upon the geometric center 52 of the turning field 54. Turned and focused beam 66b is coaxially joined with the beam 26b and directed toward a desired destination, e.g., target 62 of FIG. 3.

Figure 4:
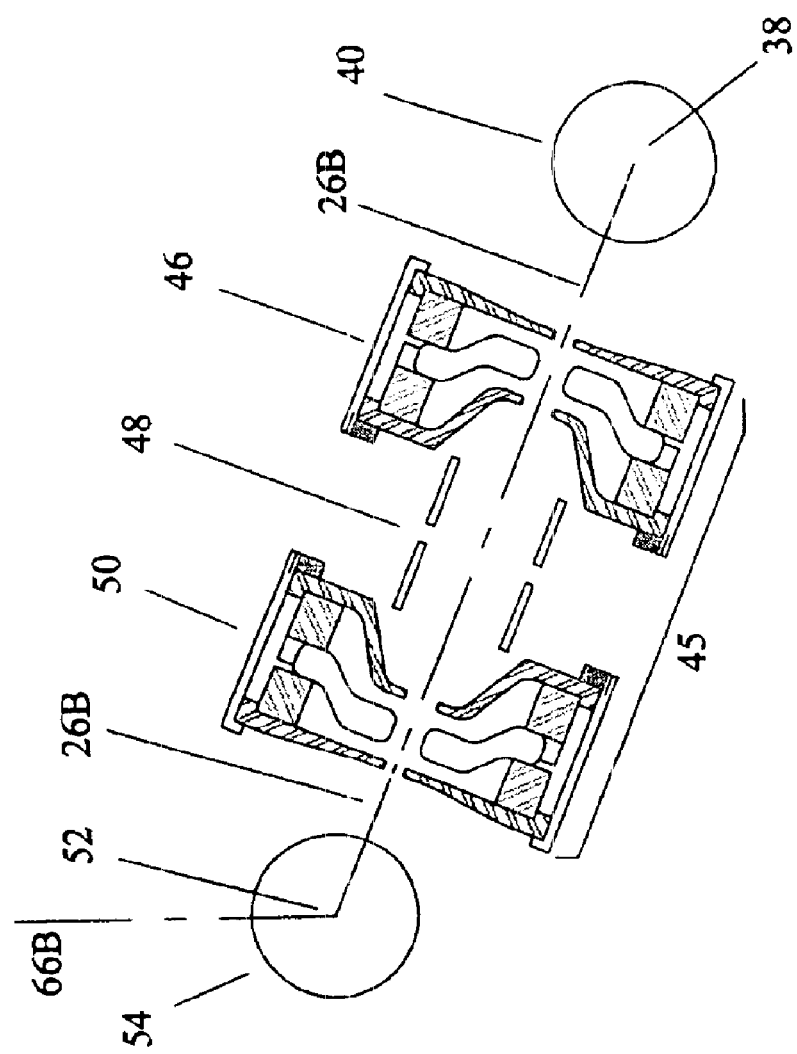
FIG. 4 is a simplified diagrammatic representation of a relay lens for separately deflecting "read" and "write" beams, as used in FIG. 3.
Figure 5:
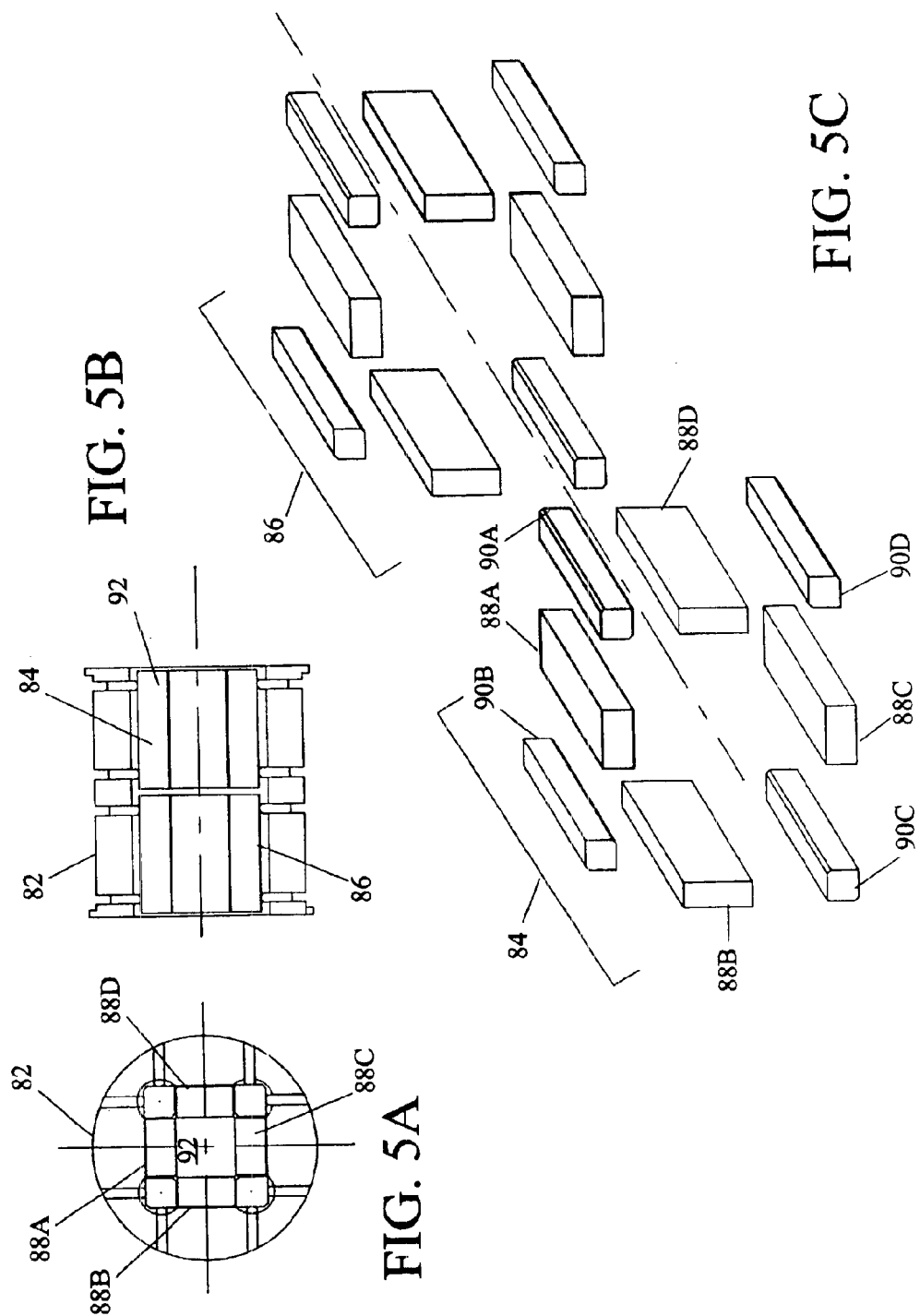
FIG. 5 is a simplified diagrammatic representation of the beam deflectors used in FIGS. 3 and 4.

FIG. 4 discloses in greater detail the preferred embodiment of relay lens structures 45 and 76. Both structures are identical, but will be described separately for clarity.

Relay lens 45 includes beam deflectors 48 therein. This enables beam 26b to be focused and manipulated independently from beam 66b so that microprecision positioning thereof on target 62 is possible to obtain the performance described hereinbefore.

Reflected beam 26b is focused upon geometric center 38 of cylindrically symmetrical magnetic turning field 40. In turn, lens 46 collimates turned beam 26b before it is passed through beam deflectors 48, and is thereafter focused by lens 50 upon geometric center 52 of turning field 54. Turned and focused beam 26b is directed toward a desired destination, e.g., target 62 of FIG. 3.

Reflected beam 66b is focused upon geometric center 72 of cylindrically symmetrical magnetic turning field 74. In turn, lens 78 collimates turned beam 66b before it is passed through beam deflectors 82, and is thereafter focused by lens 80 upon geometric center 52 of turning field 54. Turned and focused beam 66b is coaxially joined with beam 26b and directed toward a desired destination, e.g., target 62 of FIG. 3.

It will be seen by those skilled in the art that compound relay lens assembly 45 allows beam 26b to be focused at the geometric centers 38 and 52 of both turning fields 40 and 54, respectively, while being collimated as it passes through deflecting structure 45.

The relay lens assembly 76 allows beam 66b to be focused at the geometric centers 72 and 52 of both turning fields 74 and 54, respectively, while being collimated as it passes through deflecting structure 82.

A combination of assemblies 45 and 76, sharing a common magnetic turning field, permits charged particle beams to be joined coaxially when desired to accomplish certain functions not possible otherwise, as described elsewhere herein. It does not matter whether the beams have the same or opposite charges, as disclosed in FIGS. 1A–1F, or are traveling in the same or opposite directions, as disclosed in FIGS. 1A–1F.

FIG. 4 discloses the location of beam deflectors 48 and 82 in the preferred embodiment of relay lens structures 45 and 76, respectively, in which the beams 26b and 66b are collimated where beam deflection is not required, assembly may be replaced with a simple lens having object point at 38 and image pont at 54. The preferred deflection geometry s illustrated in FIG. 4 where each magnetic field deflects the beam through 63.5 degrees for a total combined deflection of 127 degrees.

FIGS. 5A–5C discloses in greater detail beam deflectors 48 and 82 as shown in FIGS. 3 and 4. These structures are useful to separately deflect monitoring and depositing beams. As these deflectors are identical, a single description will suffice for both. The description will switch between FIGS. 5A–5C, as necessary for clarity.

An insulating housing 82 (depicted in FIGS. 5A and 5B) holds two sets 84 and 86 of four uniformly electrically resistive rectangular deflection plates 88a–88d (depicted diagrammatically in FIGS. 5A–5C) spaced from one another to form square or rectangular tunnel 92 (depicted in FIG. 5A).

Plates 88a–88d are joined at the four corners thereof by electrically conducting contacts 90a–90d, as depicted in FIGS. 5A and 5C. Each contact 90a–90d is joined along two faces thereof to two resistive plates 88a–88d. As examples, contact 90a is joined on one face by plate 88a and on an adjacent face by plate 88d, and plate 90b is joined on one face by plate 88a and on an adjacent face by plate 88b, etc. The structures formed by plates 88a–88d and contacts 90a–90d from square tunnel 92 as seen from either end thereof, as depicted in FIG. 5A.

The two sets of deflectors 84 and 86 are mounted end-to-end but electrically separated. Electrical connections from the deflectors to appropriate controls and voltage sources can be made by existing techniques well-known to those skilled in the art, as can the appropriate voltages necessary to produce uniform electric deflection fields in tunnel 92 between the plates.

The foregoing described structure has several advantages, depending on the particular structure implemented. A charged particle beam traversing the deflector will experience an electric field of two-fold symmetry, which does not distort the beam or add aberrations to it. Further, the field is linear at the edges of the plates, so it will be linear where the beam passes, and will result in linear beam deflection/volt, making precision beam control possible. Finally, resistive deflecting plates will dissipate scattered electrons and ions which land on the plates, and the consequent absence of stray charges in the deflection environment is necessary for reproducible results.

The voltages on plates 88a–88c can be arranged to keep the center of tunnel 92 at ground potential, simplifying control circuitry therefor, or any other desired potential. The resulting uniform electric field can be used to produce substantially linear deflections in the charged particle beams. The two sets of plates can be used to fix the apparent center of beam deflection to any point needed.

Further, in addition to deflection voltages, voltages can be added to introduce a quadrupole moment to the beam by making the average vertical electrode potential more positive or more negative than the horizontal deflection electrodes. This feature permits compensation for the so-called "deflection aberration" due to different parts of the beam traversing the deflector at differing average voltages, and hence differing velocities, resulting in a focusing of the beam in the direction of deflection. This compensation would need to be achieved in a separate structure in other type deflectors.

When two or more charged particle beams are to be joined at some point in the system, e.g., as described and disclosed hereinbefore in connection with FIG. 3, beam deflectors should be located prior to—"upstream from"—the joining magnetic field, e.g. as described and disclosed hereinbefore in connection with FIG. 4, if the separate beams are to be deflected independently simultaneously.

Figure 6:
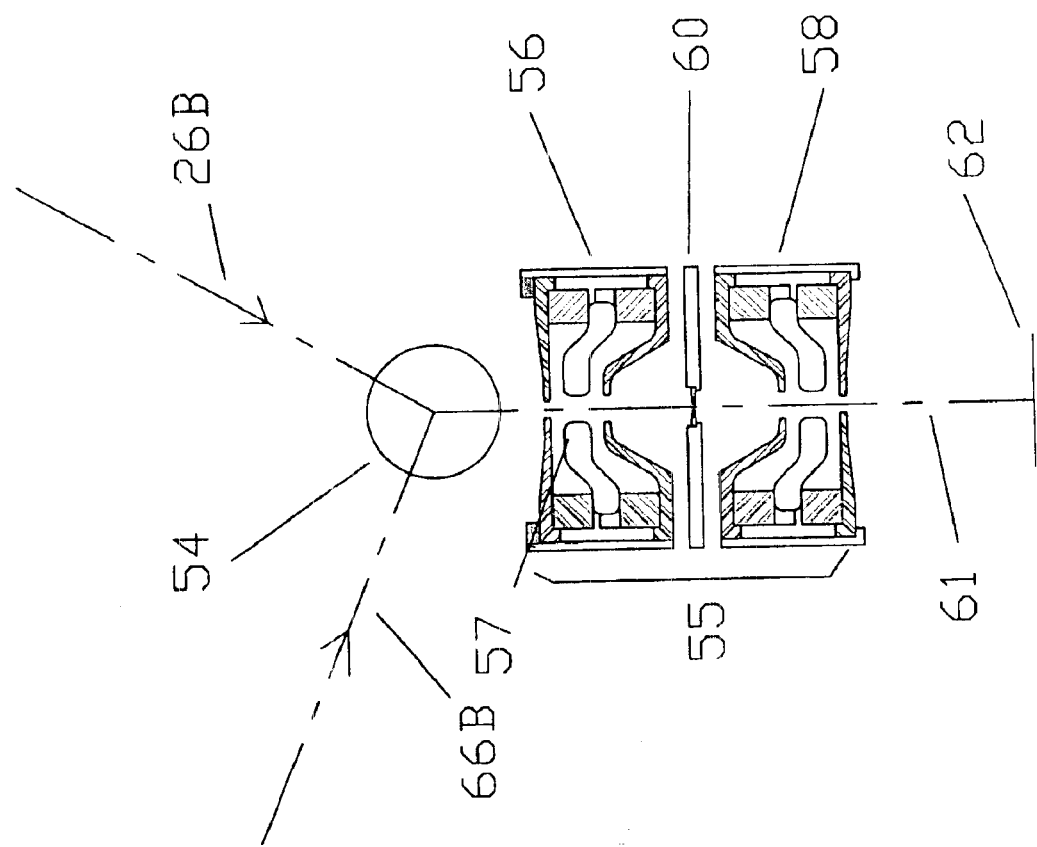
FIG. 6 discloses a compact spatial arrangement of two electrostatic lenses, a magnetic field, and a mirror.

FIG. 6 discloses arrangement 55, as seen hereinbefore, of symmetrically cylindrical magnetic turning field 54 joining two separate beams 26b and 66b, of charged particles having different charge to mass ratios, and two separate electrostatic lenses 56 and 58, focusing the two beams 26b and 66b into a coaxial beam 61 at a common point on target 62.

Three electrode, electrostatic lenses (also known as Einzel lenses), exemplified by lenses 56 and 58, will focus either electrons or ions with either a positive or negative potential on center electrodes 57 and 59, of lens 56 and 58, respectively. What has not been known heretofore is that there is a unique voltage which can be placed on center electrode 57 and 59, of lens 56 and 58, respectively, which will simultaneously focus negative electrons of one energy and positive ions of another energy at the same point and in the same plane.

The preferred embodiment will focus an electron beam and an ion beam, simultaneously, with the same lens at the same time. Consequently, any ion species may be used with an electron beam, since all ion beams of the same energy are focused similarly. Further, the beams do not have to be traveling through the lens in the same direction to obtain the same results, as explained hereinbefore.

Further, this mode of operation is not limited to unipotential lenses. A substantial range of accelerating or decelerating electrostatic lenses exhibits the same properties. All unipotential lenses, accelerating or decelerating, may be composed of any number of electrodes or electrode shapes. This feature also permits the use of compound lenses to be used with a telecentric stop as shown in FIG. 6.

For example, the optical system of FIG. 6 is composed of two electrostatic lenses each having the characteristic of focusing two different charged particle beams having different charge-to-mass ratios and different energies. Unipotential lenses 56 and 58 will simultaneously image beam 26b of 15 kV electrons and beam 66b of 5 kV positive gallium ions apparently emanating from the geometric center 52 of magnetic field 54, and join them in a common coaxial beam 26b+66b through telecentric aperture stop 60. To obtain identical lens strengths for both beams, a negative voltage beam 26b–66b through telecentric aperture stop 60. To obtain identical lens strengths for both beams, a negative voltage of −10.5 kV, applied to center electrode 57 and 59 of lens 56 and 58, respectively, will produce equal strengths for the positive and negative components of coaxial beam 26b+66b. This voltage is about 70% of 26b voltage−15 kv and about−210% of 66b voltage. The lens acts in the so-called accelerating mode for the ions, and in the decelerating mode for the electrons, to produce the same lens strength for the two components of coaxial beam 26b+66b (an electrostatic lens is generally weaker in the accelerating mode than in the decelerating mode).

Lens 58 receives the combined coaxial collimated beam 26b+66b from stop 60 and produces a simultaneous and coincident image of ion beam 26b and electron beam 66b on the target plane 62. If stop 60 is placed in the focal plane of lens 58, the optical system of FIG. 6 is capable of providing independent control of electron beam 66b and ion beam 26b which are perpendicular (or substantially perpendicular) to the target plane 62 when it is desirable to scan the beams. An appropriate deflection optical geometry, such as disclosed in FIG. 4, should be used to avoid other troublesome aberrations.

A further use of this structure can be made by combining it with a cylindrically symmetrical magnetic joining field, such a disclosed in FIG. 1A. Since the magnet turns a charged particle beam through an angle proportional to the square root of the charge-to-mass ratio, there is the possibility of joining not only two beams with opposite sign charge-to-mass ratios, but also two or more charge-to-mass ratios with the same sign charge-to-mass ratios. Coincident beams of different charge-to-mass ratios but same sign charge-to-mass ratios will be focused similarly by any subsequent electrostatic lens as long as the energy of the beams is the same. Two or more joining magnets may be cascaded to provide a plurality of ions to the target plane. This may be useful in the deposition of alloys where simultaneous deposition of multiple elements is desired.

Even further, cylindrical joining magnets may be used to combine both positive and negative ions in a single beam, which may be important in the construction of insulators and certain chemicals.

It is noted that the charged particles emanating from the target may be varied. For example the particles may be the reflected beam and/or particles, secondary electrons, secondary ions, etc.

Use can be made of both (1) the lens simultaneously passing and focusing in both directions and (2) the simultaneous joining and separating ability of the cylindrical magnet. Ions may be placed on a surface while an electron beam is simultaneously probing the process. Both electrons and ions expelled from the work pass back through the lens and magnet and are separated, allowing individual detection of the returning species. This is helpful for aligning, monitoring, and manipulating of individual atoms or molecules, and in analytical analysis.

Figure 7:
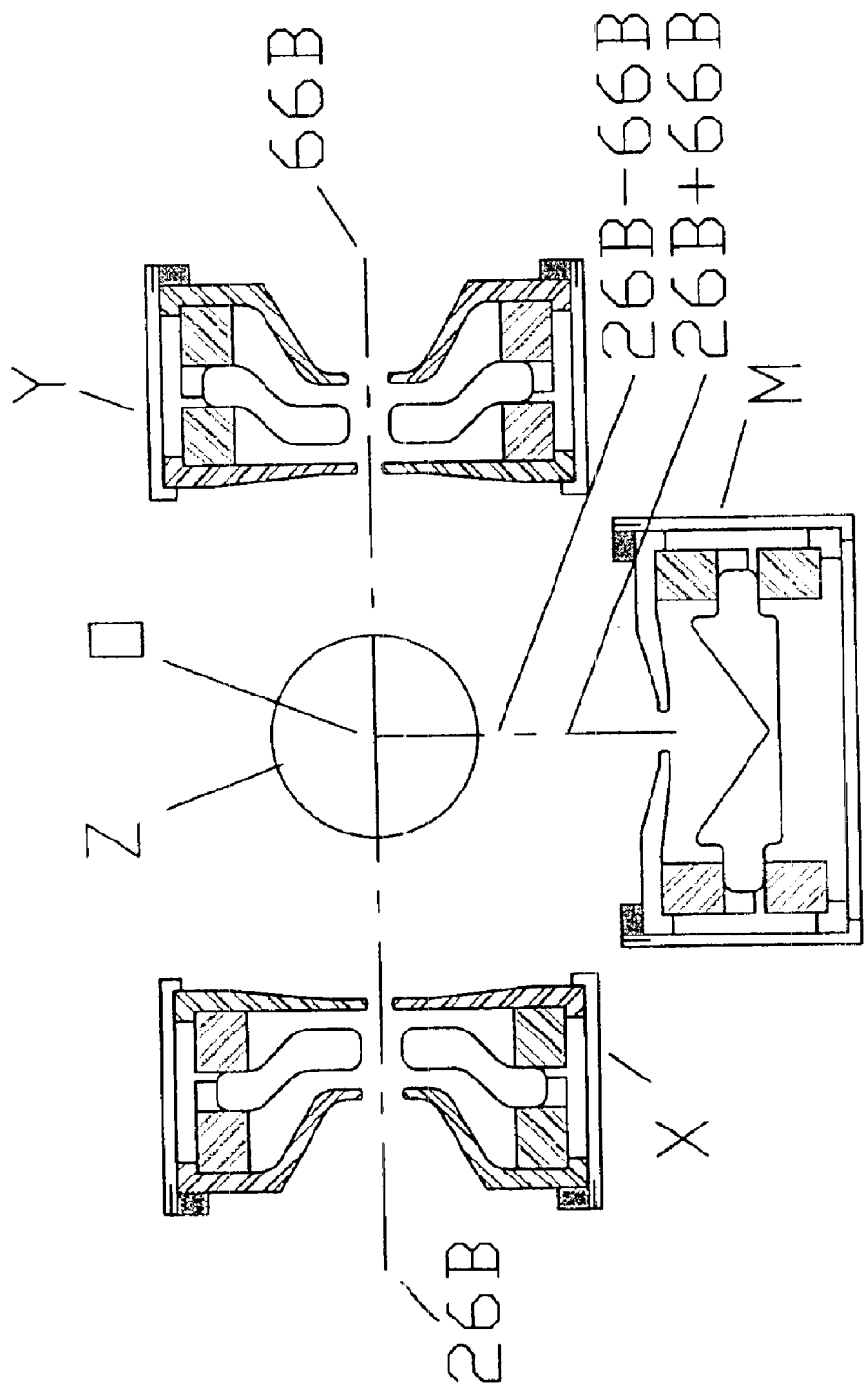
FIG. 7 discloses an arrangement of a magnetic field for joining separate beams of charged particles, and two lenses focusing beams on a target.

FIG. 7 discloses an arrangement of two electrostatic lenses X and Y, cylindrically symmetrical magnetic turning field Z, and electrostatic mirror M, in which the angles and are 90 degrees. The separate axes of X, Y, and M pass through the geometric center O of turning field Z, and the beam passing through all three optical elements X, Y, and Z is also focused at the geometric center O, making it possible to produce the system of FIG. 3 in a small physical space. Mirror M is shaped and biased to have external focal point 0, and to cancel the spherical and chromatic aberrations introduced into beam 26b+66b by lenses X and Y, as well as by any other lenses in the system, by introducing overcorrecting spherical and chromatic aberrations of opposite sign thereto into the beam. Because only one magnetic turning field Z is involved, all axes lie in a common plane, lending its use to a more economical and compact physical structure than that of FIG. 3. The preferred angle is 90 degrees, but other angles may likewise be employed, as desired.

Suggestion has been made herein before that work of molecular and atomic dimension would be possible under the appropriate circumstances. The following facts give some idea of the possible dimensional resolutions possible.

With both ion and electron beams completely corrected for spherical and chromatic aberration, an electron beam energy of two kilovolts (2 kV) gives an electron wavelength of 0.27 angstroms (A). The theoretical resolution limit for such an electron beam in an aberration-corrected electron optical system would be 1.67 A for an angular aperture of 100 milliradians (mrad), and 16.7 A for 10 mrad angular aperture. Published results of experiments conducted earlier by the present inventor completely corrected an electron beam from a 35 mrad angular aperture, and unpublished results of later experiments indicate complete correction of a 100 mrad beam could be achieved under certain circumstances. A beam of 8 kV electrons would give resolutions of one-half these numbers.

Ions have a much shorter wavelength than electrons making atomic resolution possible with smaller beam energies, e.g., 330 eV gallium ions have a wavelength of 0.002 A, and the corresponding resolution would be 0.12 A for a beam from a 10 mrad angular aperture. Ions from a beam of 300 eV and below have a reasonable probability of adhering to a target, e.g., a substrate, giving a resolution of 0.1 the dimension of the smallest atom, and making possible subatomic placement of ions, and the building of so-called "designer" molecules.

One potential use of the apparatus of the present invention is the depositing of a single atom (such as an ion) on a substrate, and the moving into position of that atom—"nudging"—by a stream of electrons, while simultaneously observing the process.

Another use of the apparatus of the present invention is the use of an ion beam to "sputter off" the surface of a compound to chemically map the surface thereof.

More specifically, referring to FIG. 3, the focusing and deflecting functions disclosed herein theoretically make it possible to place molecular-sized, or even simple ion deposits with ion beam 26a, 26b, and simultaneously to scan, or read, with electron beam 66a, 66b what is being deposited thereon.

Further, an electron beam could be used to erode the molecular-sized deposits into desired shapes, and/or to obtain the single ion deposits.

The correction of chromatic and spherical aberration in writing and reading beams, permits a reduction in size of individual integrated semiconductor devices by several orders of magnitude, and a consequent substantial increase in density and/or speed of integrated circuits.

In the field of "nano-electronics", one of the obstacles to research and development and, consequently progress therein, has been the lack of manufacturing processes and tools to investigate the physics of small devices. The system diagrammatically depicted in FIG. 3, and described in connection therewith, could be used to fabricate "nanometer-dimension" electronic circuits directly from constituent materials. Conductor runs could be directly deposited without the aid of lithographs. Insulators could be grown in place only where they were needed, from a layer of silicon deposited on a substrate, and subsequently converted to oxide with the aid of an oxygen ion beam. Direct "doping" could be performed in place by either "driving" ions in place directly, or by first depositing them on the desired surface and "driving", or melting, them with a directed electron beam. A substantial improvement in semiconductor electronic production could be achieved by the virtual elimination of toxic waste byproducts, since only materials needed to layout the circuits or devices would deposited in the disposition process described herein. Little or no etching or dissolving, with their toxic waste byproducts, would be generated.

All manufacturing of such devices and materials could be done without removing the work from the system. Once a circuit was completed, connections could be made to power and test instrument terminals fabricated in the system and the circuit could be evaluated in place. Imaging of the circuit in a diagnostic mode during testing could be performed by e.g., scanning with a low energy electron beam or an ion beam in a "mirror" mode. Modifications of the circuit could be made with ion beams in place. When final circuit performance and configuration was satisfactorily obtained, it could be reproduced automatically and indefinitely by a "step-and-repeat" process.

A significant obstacle to nano device investigation and manufacturing is the alignment from one step in a process to the next. By simultaneously reading and writing along a coaxial optical axis these limitations are overcome. An indefinite array of structures may be "stitched" together with sub-atomic precision.

Automatic fabrication of an endless variety of devices would be possible with the simultaneous "read/write" system disclosed in FIG. 3 and described in connection therewith. Alignment and registration could be controlled automatically, permitting the system to manufacture devices of unlimited size and complexity by joining the "fields" together. Fields of interest which already exist for molecular-sized devices are biology, medicine, mechanics, ecology, chemistry, physics, and electronics.

It is not often realized that, as the size of devices is reduced beyond a certain point, serial production of some devices becomes not only feasible but economically desirable when compared to parallel production. Liquid metal and gas-field ion sources are extremely bright, and provide more than sufficient current to build nanodevices economically if the beams from these sources can be corrected for spherical and chromatic aberration as disclosed herein.

In addition to providing improved resolution, the preferred embodiment, by permitting aberration-corrected beams to be manipulated, also increases the angular size of the beams to be increased, providing increased beam current and throughput. This feature is of use in improving speed and resolution of existing instruments such as scanning electron microscopes, transmission electron microscopes, photo emission microscopes, low energy emission microscopes, and other analytical instruments. Further, optical lithography mask-making and repair would be benefitted thereby.

The terms and expressions which have been employed in the foregoing specification are used therein as terms of description and not of limitation, and there is no intention, in the use of such terms and expressions, of excluding equivalents of the features shown and described, or portions thereof, it being recognized that the scope of the invention is defined and limited only by the claims which follow.

What is claimed is:

1. A method for aligning at least two beams of particles, comprising:
   (a) directing a first beam along a first axis into a field where said first beam exits said field along a second axis; and
   (b) directing a second beam along a third axis into said field where said second beam exists said field along a fourth axis, said third axis is at least one of colinear and coaxial with said second axis and said second beam along said third axis has a different direction of travel than said first beam along said second axis.

2. The method of claim 1 wherein said field is a magnetic field having a geometric center thereto.

3. The method of claim 2 wherein said first beam is focused upon said geometric center.

4. The method of claim 3 wherein said second beam is focused upon said geometric center.

5. The method of claim 4 wherein said first and fourth axes are not coaxial.

6. The method of claim 5 wherein said first and fourth axes are not colinear.

7. The method of claim 1 wherein said second and third axes are coaxial.

8. The method of claim 1 wherein said second and third axes are colinear.

9. The method of claim 1 wherein said field is cylindrical magnetic field.

10. The method of claim 1 wherein said field is a magnetic field having a substantially symmetrical cylindrical form having a geometric center thereto upon which said beams are focused.

11. An apparatus that co-axially aligns at least two beams of charged particles, comprising:
    (a) a field;
    (b) a first beam directed along a first axis into said field;
    (c) a second beam directed along a second axis into said field; and
    (d) whereby said first and second beams are co-axially aligned, by interaction between said field and said first and second beams, into a third beam directed along a third axis.

12. The apparatus of claim 11 wherein said field is a magnetic field having a geometric center thereto.

13. The apparatus of claim 12 wherein said first beam is focused upon said geometric center.

14. The apparatus of claim 13 wherein said second beam is focused upon said geometric center.

15. The apparatus of claim 14 wherein said third beam is at least one of colinear and coaxial.

16. The apparatus of claim 15 wherein said magnetic field is cylindrical.

17. The apparatus of claim 11 wherein said field is a magnetic field having a substantially symmetrical cylindrical form having a geometric center thereto upon which said beams are focused.

* * * * *